US010406097B2

(12) United States Patent
Thorel et al.

(10) Patent No.: US 10,406,097 B2
(45) Date of Patent: Sep. 10, 2019

(54) **EXTRACT OF *ARTHROBACTER AGILIS* FOR USE IN PARTICULAR IN COSMETICS**

(71) Applicant: Jean-Noël Thorel, Paris (FR)

(72) Inventors: Jean-Noël Thorel, Paris (FR); François-Xavier Pellay, Meudon la Forêt (FR)

(73) Assignee: Jean Noël-Thorel, Paris (FR)

( * ) Notice: Subject to any disclaimer, the term of this patent is extended or adjusted under 35 U.S.C. 154(b) by 852 days.

(21) Appl. No.: 14/779,410

(22) PCT Filed: Apr. 9, 2014

(86) PCT No.: PCT/FR2014/050852
§ 371 (c)(1),
(2) Date: Sep. 23, 2015

(87) PCT Pub. No.: WO2014/167247
PCT Pub. Date: Oct. 16, 2014

(65) Prior Publication Data
US 2016/0113864 A1    Apr. 28, 2016

(30) Foreign Application Priority Data

Apr. 9, 2013  (FR) ...................................... 13 53200

(51) Int. Cl.
*A61K 8/99* (2017.01)
*A61K 8/31* (2006.01)
*A61Q 17/04* (2006.01)
*A61Q 19/00* (2006.01)
*A61Q 19/08* (2006.01)

(52) U.S. Cl.
CPC .................. *A61K 8/99* (2013.01); *A61K 8/31* (2013.01); *A61Q 17/04* (2013.01); *A61Q 19/004* (2013.01); *A61Q 19/08* (2013.01); *A61K 2800/522* (2013.01)

(58) Field of Classification Search
CPC .... A61K 2300/00; A61K 31/728; A61K 8/60; A61K 45/06; A61K 8/44; A61K 8/606; A61K 8/64; A61K 31/401; A61K 33/00; A61K 8/19; A61K 8/23; A61K 8/27; A61K 8/673; A61K 8/675; A61K 8/345; A61K 8/365; A61K 31/70; A61K 31/7052; A61K 8/20; A61K 8/24; A61K 8/25; A61K 8/34; A61K 8/41; A61K 8/442; A61K 8/447; A61K 8/49; A61K 8/4913; A61K 8/492; A61K 8/494; A61K 8/4946; A61K 8/4986; A61K 8/55; A61K 8/67; A61K 8/735; A61K 31/235; A61K 31/375; A61K 31/7004; A61K 31/727; A61K 31/737; A61K 38/08; A61K 38/34; A61K 38/40; A61K 38/44; A61K 38/446; A61K 38/465; A61K 38/57; A61K 8/66; A61K 8/676; A61K 9/0019; A61K 2800/522; A61K 2800/85; A61K 2800/91; A61K 47/02; A61K 47/18; A61K 8/29; A61K 8/42; A61K 8/553; A61K 8/63; A61K 8/678; A61K 9/0014; A61K 9/0048; A61K 2800/59; A61K 2800/75; A61K 31/05; A61K 31/085; A61K 31/19; A61K 31/20; A61K 31/201; A61K 36/16; A61K 36/185; A61K 38/06; A61K 8/31; A61K 8/347; A61K 8/37; A61K 8/498; A61K 8/602; A61K 8/645; A61K 8/97; A61K 8/99; A61Q 19/00; A61Q 19/08; A61Q 17/04; A61Q 19/008; A61Q 1/14; A61Q 19/004; A61Q 19/007; A61Q 19/10; A61Q 5/00; A61Q 7/00; A61Q 19/005; A61Q 19/04; A61Q 19/06; A61L 27/20; A61L 2400/06; A61L 27/52; C08L 5/08; C12N 2500/95; C12N 5/0629; C12N 2501/905; C12N 5/0656
See application file for complete search history.

(56) References Cited

U.S. PATENT DOCUMENTS 9,707,417 B2 *  7/2017  Wagner .................... A61K 8/35
2011/0123468 A1 *  5/2011  Wagner .................... A61K 8/35
                                                          424/59

FOREIGN PATENT DOCUMENTS

JP    7-132096 A    5/1995
WO   00/24369 A1    5/2000

OTHER PUBLICATIONS

Fong NJC, Burgess ML, Barrow KD, Glenn DR "Carotenoid Accumulation in the Psychrotrophic Bacterium *Arthrobacter agilis* in Response to Thermal and Salt Stress" Appl. Microbiol. Biotechnol., Jul. 26, 2001, 56, 750-756: DOI 10.1007/s002530100739. (Year : 2001).*
Jagannadham MV, et al The Major Carotenoid Pigment of a Psychrotrophic Micrococcus roseus Strain: Purification, Structure, and Interaction with Synthetic Membranes Journal of Bacteriology, Dec. 1991,173(24),pp. 7911-7917. (Year: 1991).*
Korthals HJ, et al "Separation and quantification of pigments from natural phototrophic microbial populations" FEMS—Microbiol. Ecol. (FEMS Microbiol. Lett.),1985,31(3),pp. 177-185; doi.org/10.1016/0378-1097(85)90019-9. (Year: 1985).*
Mukai, Kazuo "Synthesis and Kinetic Study of Antioxidant and Prooxidant Actions of Vitamin E Derivatives" Vit. E in Health and Disease, Chapter 8, 1993, pp. 97-119. (Year: 1993).*

(Continued)

*Primary Examiner* — Aaron J Kosar
(74) *Attorney, Agent, or Firm* — Seed IP Law Group LLP

(57) ABSTRACT

Cosmetic, pharmaceutical or dietary composition comprising an extract of the bacteria *Arthrobacter agilis*, preferably rich in carotenoids.

14 Claims, 5 Drawing Sheets
Specification includes a Sequence Listing.

(56) References Cited

OTHER PUBLICATIONS

Database GNPD (Online) Bolaiya Cosmetics, "Shining Star Eye Cream," XP-002732012, Database Accession No. 1305663, (4 pages) (Apr. 2010).
Database GNPD (Online) Ecco Bella Botanicals, "M.D. Formulated Age Antidote Day Cream," XP-002732011, Database Accession No. 10194702, (2 pages) (Nov. 2004).
Database GNPD (Online) Parafarm, "Dietary Supplement," XP-002732013, Database Accession No. 1230777, (2 pages) (Jan. 2010).
Database WPI, XP-002717875, KR20120068367, Accession No. 2012-H70470, Thomson Scientific, London, GB, (one page) (Jun. 27, 2012).
Dieser et al., "Carotenoid Pigmentation in Antarctic Heterotrophic Bacteria as a Strategy to Withstand Environmental Stresses," *Arctic, Antarctic and Alpine Research* 42(4):396-405 (2010).
Fong et al., "Carotenoid accumulation in the psychrotrophic bacterium *Arthrobacter agillis* in response to thermal and salt stress," *Appl MicrobiolBiotechnol*. 56:750-756 (2001).
Koch et al., "Reclassification of *Micrococcus agilis* (Ali-Cohen 1889) to the Genus *Arthrobacter* as *Arthrobacter agilis* comb. nov. and Emendation of the Genus *Arthrobacter*," *International Journal of Systematic Bacteriology* 45(4):837-839 (Oct. 1995).
Krinsky, "Antioxidant Functions of Carotenoids," *Free Radical Biology & Medicine* 7:617-635 (1989).
Meckel et al., "Extractability of Carotenoid Pigments from Non-photosynthetic Bacteria with Solvents and Detergents: Implications for the Location and Binding of the Pigments," *Journal of General Microbiology* 120:111-116 (1980).
Ostling et al., "Microelectrophoretic Study of Radiation-Induced DNA Damages in Individual Mammalian Cells," *Biochemical and Biophysical Research Communications* 123(1):291-298 (Aug. 30, 1984).
Re et al., "Antioxidant activity applying an improved ABTS radical cation decolorization assay," *Free Radic Biol Med*. 26(9-10):1231-1237, (1 page), Abstract (May 1999).
Saito et al., "Hydroxyl Radical Scavenging Ability of Bacterioruberin," *Radiat. Phys. Chem*. 50(3):267-269 (1997).
Saperstein et al, "Association of Carotenoid Pigments with Protein Components in Non-Photosynthetic Bacteria," *Biochimica et Biophysica Acta* 16:482-488 (1955).
Singh et al., "A simple technique for quantitation of low levels of DNA damage in individual cells," *Experimental Cell Research* 175(1):184-191, (1 page), Abstract (Mar. 1, 1968).

\* cited by examiner

SEQUENCE LISTING

```
<160> NUMBER OF SEQ ID NOS: 2

<210> SEQ ID NO 1
<211> LENGTH: 1482
<212> TYPE: DNA
<213> ORGANISM: Arthrobacter sp.

<400> SEQUENCE: 1
gatcctggct caggatgaac gctggcggcg tgcttaacac atgcaagtcg aacgatgaac      60
ctcacttgtg gggggattag tggcgaacgg gtgagtaaca cgtgagtaac ctgcccttga     120
ctctgggata agcctgggaa accgggtcta atactggata cgaccttctg gcgcatgcca     180
tgttggtgga aagcttttgt ggttttggat ggactcgcgg cctatcagct tgttggtggg     240
gtaatggcct accaaggcga cgacgggtag ccggcctgag agggtgaccg gccacactgg     300
```

-continued

```
gactgagaca cggcccagac tcctacggga ggcagcagtg gggaatattg cacaatgggc    360
gcaagcctga tgcagcgacg ccgcgtgagg gatgaaggcc ttcgggttgt aaacctcttt    420
cagtagggaa gaagcctgtc ttttgggtgg gtgacggtac ctgcagaaga agcgccggct    480
aactacgtgc cagcagccgc ggtaatacgt agggcgcaag cgttatccgg aattattggg    540
cgtaaagagc tcgtaggcgg tttgtcgcgt ctgccgtgaa agtccggggc ttaactccgg    600
atctgcggtg ggtacgggca gactagagtg cagtagggga gactggaatt cctggtgtag    660
cggtgaaatg cgcagatatc aggaggaaca ccgatggcga aggcaggtct ctgggctgta    720
actgacgctg aggagcgaaa gcatgggag cgaacaggat tagataccct ggtagtccat     780
gccgtaaacg ttgggcacta ggtgtggggg acattccacg ttttccgcgc cgtagctaac    840
gcattaagtg ccccgcctgg ggagtacggc cgcaaggcta aaactcaaag gaattgacgg    900
gggcccgcac aagcggcgga gcatgcggat taattcgatg caacgcgaag aaccttacca    960
aggcttgaca tgaaccggaa tgatgcagag atgtgtcagc cacttgtggc cggtttacag   1020
gtggtgcatg gttgtcgtca gctcgtgtcg tgagatgttg ggttaagtcc cgcaacgagc   1080
gcaaccctcg ttccatgttg ccagcgggtt atgccgggga ctcatgggag actgccgggg   1140
tcaactcgga ggaaggtggg gacgacgtca atcatcatg cccttatgt cttgggcttc     1200 acgcatgcta caatggccgg tacaaagggt tgcgatactg tgaggtggag ctaatcccaa   1260
aaagccggtc tcagttcgga ttgaggtctg caactcgacc tcatgaagtt ggagtcgcta   1320
gtaatcgcag atcagcaacg ctgcggtgaa tacgttcccg ggccttgtac acaccgcccg   1380
tcaagtcacg aaagttggta cacccgaag ccggtggcct aaccccttgt gggagggagc    1440
cgtcgaaggt gggaccggcg attgggacta agtcgtaaca ag                      1482
```

<210> SEQ ID NO 2
<211> LENGTH: 1400
<212> TYPE: DNA
<213> ORGANISM: Arthrobacter sp.
<220> FEATURE:
<221> NAME/KEY: misc_feature
<222> LOCATION: (571)...(571)
<223> OTHER INFORMATION: n = A,T,C or G
<220> FEATURE:
<221> NAME/KEY: misc_feature
<222> LOCATION: (671)...(671)
<223> OTHER INFORMATION: n = A,T,C or G
<220> FEATURE:
<221> NAME/KEY: misc_feature
<222> LOCATION: (1358)...(1358)
<223> OTHER INFORMATION: n = A,T,C or G
<220> FEATURE:
<221> NAME/KEY: misc_feature
<222> LOCATION: (1376)...(1376)
<223> OTHER INFORMATION: n = A,T,C or G
<220> FEATURE:
<221> NAME/KEY: misc_feature
<222> LOCATION: (1390)...(1390)
<223> OTHER INFORMATION: n = A,T,C or G

<400> SEQUENCE: 2

```
acatgcaagt cgaacgatga acctcacttg tgggggatt agtggcgaac gggtgagtaa      60
cacgtgagta acctgccctt gactctggga taagcctggg aaaccgggtc taatactgga   120
tacgaccttc tggcgcatgc catgttggtg gaaagctttt gtggttttgg atggactcgc   180
ggcctatcag cttgttggtg gggtaatggc ctaccaaggc gacgacgggt agccggcctg   240
agagggtgac cggccacact gggactgaga cacggcccag actcctacgg gaggcagcag   300
```

```
tggggaatat tgcacaatgg gcgcaagcct gatgcagcga cgccgcgtga gggatgaagg    360
ccttcgggtt gtaaacctct ttcagtaggg aagaagccgg cctttttgggt tggtgacggt   420 acctgcagaa gaagcgccgg ctaactacgt gccagcagcc gcggtaatac gtagggcgca    480
agcgttatcc ggaattattg ggcgtaaaga gctcgtaggc ggtttgtcgc gtctgccgtg    540
aaagtccggg gcttaactcc ggatctgcgg ngggtacggg cagactagag tgcagtaggg    600
gagactggaa ttcctggtgt agcggtgaaa tgcgcagata tcaggaggaa caccgatggc    660
gaaggcaggt ntctgggctg taactgacgc tgaggagcga aagcatgggg agcgaacagg    720
attagatacc ctggtagtcc atgccgtaaa cgttgggcac taggtgtggg ggacattcca    780
cgttttccgc gccgtagcta acgcattaag tgccccgcct ggggagtacg gccgcaaggc    840
taaaactcaa aggaattgac gggggcccgc acaagcggcg gagcatgcgg attaattcga    900
tgcaacgcga agaaccttac caaggcttga catgaaccgg aatgatgcag agatgtgtca    960
gccacttgtg gccggtttac aggtggtgca tggttgtcgt cagctcgtgt cgtgagatgt   1020
tgggttaagt cccgcaacga gcgcaaccct cgttccatgt tgccagcggg ttatgccggg   1080
gactcatggg agactgccgg ggtcaactcg gaggaaggtg gggacgacgt caaatcatca   1140 tgcccttat gtcttgggct tcacgcatgc tacaatggcc ggtacaaagg gttgcgatac    1200
tgtgaggtgg agctaatccc aaaaagccgg tctcagttcg gattgaggtc tgcaactcga   1260
cctcatgaag ttggagtcgc tagtaatcgc agatcagcaa cgctgcggtg aatacgttcc   1320
cgggccttgt acacaccgcc cgtcaagtca cgaaagtngt aacacccgaa gccggngcct   1380
aaccccttgn ggagggagcc                                              1400
```

EXTRACT OF *ARTHROBACTER AGILIS* FOR USE IN PARTICULAR IN COSMETICS

STATEMENT REGARDING SEQUENCE LISTING

The Sequence Listing associated with this application is provided in text format in lieu of a paper copy, and is hereby incorporated by reference into the specification. The name of the text file containing the Sequence Listing is 900237_401USPC_SEQUENCE_LISTING.txt. The text file is 4.5 KB, was created on Dec. 17, 2015, and is being submitted electronically via EFS-Web.

FIELD OF THE INVENTION

The present invention relates to an extract of *Arthrobacter agilis* for use in particular in cosmetics, and more specifically an extract rich in carotenoids.

Specifically, the invention relies on the detection of the protection of proteins against free oxygen radicals (ROS) and radiation of light (UV and visible) by such an extract, to fight against the alteration of cells, particularly that of the skin, caused by external aggressions. Such an extract, optionally in combination with other antioxidants, therefore help fight against oxidative stress including cellular ageing.

PRIOR ART

In aerobic organisms, including humans, oxygen is necessary for survival but is also responsible for oxidative damage related to its reactive metabolites. Thus, the term ROS ("reactive oxygen species") or ROM ("reactive oxygen metabolites") is commonly used to refer to all the free radicals and non-radical chemical species that are involved in oxidative biological processes and an excess of which is considered as the basis of an increasing number of degenerative processes and diseases. More specifically, the term ROS includes the superoxide radical anion $O_2^-$., hydroxyl radical OH., singlet oxygen $^1O_2$ and hydrogen peroxide $H_2O_2$ as well as alkoxy radicals RO. and peroxy radicals ROO., which are formed from organic molecules in the oxidative processes. The production of exogenous origin of these metabolites essentially depends on physical events, such as ultraviolet radiation (UV) or chemical events such as xenobiotics. Endogenous production, in turn, is mainly due to the leakage of electrons in the respiratory chain in the mitochondria.

Regardless of their formation process, these metabolites are dangerous to the body because of their high reactivity and their action affects various cellular components, which include a large number of structural proteins, enzymes, amino acids, DNA and RNA, carbohydrates, and lipids and phospholipids.

Note that in the case of UV radiation, other than the generation of reactive species, there may be more direct physical damage to the cellular components. Thus, the UV are known to induce thymine dimers that may cause mutations, or breaks in the DNA.

In case of excessive production of reactive metabolites, the body is faced with a process called "oxidative stress".

To defend itself against the damage caused by these metabolites, the body has developed defence systems against oxidation in order to decrease the reactivity of these substances or to neutralise them. These systems may be proteic, such as serum albumin (HSA), superoxide dismutase (SOD), catalase, peroxidases or small peptides, or non-proteic, such as ubiquinol, anthocyanins, flavonoids, liposoluble vitamins (for example vitamin A and E) and water-soluble vitamins (for example vitamin C). The cells also have repair systems and systems for degradation of oxidized molecules.

Thus, to fight against oxidative stress, it is advisable to adopt a diet rich in naturally antioxidant substances and take medications or food supplements containing vitamins capable of neutralising the reactive species. In the cosmetic field, antioxidants are incorporated in many products to help fight against premature ageing due to oxidative stress.

Therefore, the search for new molecules or new extracts with antioxidant activity, to be incorporated into dietary supplements or cosmetic compositions, has been for many years a major challenge.

DESCRIPTION OF THE INVENTION

The present invention relies on the identification of an extract derived from an extremophilic bacterium, having substantial antioxidant activity. Other than a direct effect on the free radicals, this present application indicates a particular effect of such an extract on the damage caused by UV or visible light, and more generally a protective or stabilising effect on proteins as well as a synergy with known antioxidants.

Thus, the present invention relates to an extract of the bacterium *Arthrobacter agilis*, more specifically an extract rich in carotenoids obtained from this bacterium.

The bacterium *Arthrobacter agilis* has been described, for example, by Koch et al. (*Int J Syst Bacteriol.* 1995, 45(4): 837-9) and can be easily identified, thanks to the sequence of its 16S RNA available in the databases under the number X80748 and corresponding to the sequence SEQ ID NO: 1 hereafter:

```
GATCCTGGCT CAGGATGAAC GCTGGCGGCG TGCTTAACAC

ATGCAAGTCG AACGATGAAC CTCACTTGTG GGGGGATTAG

TGGCGAACGG GTGAGTAACA CGTGAGTAAC CTGCCCTTGA

CTCTGGGATA AGCCTGGGAA ACCGGGTCTA ATACTGGATA

CGACCTTCTG GCGCATGCCA TGTTGGTGGA AAGCTTTTGT

GGTTTTGGAT GGACTCGCGG CCTATCAGCT TGTTGGTGGG

GTAATGGCCT ACCAAGGCGA CGACGGGTAG CCGGCCTGAG

AGGGTGACCG GCCACACTGG GACTGAGACA CGGCCCAGAC

TCCTACGGGA GGCAGCAGTG GGGAATATTG CACAATGGGC

GCAAGCCTGA TGCAGCGACG CCGCGTGAGG GATGAAGGCC

TTCGGGTTGT AAACCTCTTT CAGTAGGGAA GAAGCCTGTC

TTTTGGGTGG GTGACGGTAC CTGCAGAAGA AGCGCCGGCT

AACTACGTGC CAGCAGCCGC GGTAATACGT AGGGCGCAAG

CGTTATCCGG AATTATTGGG CGTAAAGAGC TCGTAGGCGG

TTTGTCGCGT CTGCCGTGAA AGTCCGGGGC TTAACTCCGG

ATCTGCGGTG GGTACGGGCA GACTAGAGTG CAGTAGGGGA

GACTGGAATT CCTGGTGTAG CGGTGAAATG CGCAGATATC

AGGAGGAACA CCGATGGCGA AGGCAGGTCT CTGGGCTGTA
```

-continued

```
ACTGACGCTG AGGAGCGAAA GCATGGGGAG CGAACAGGAT

TAGATACCCT GGTAGTCCAT GCCGTAAACG TTGGGCACTA

GGTGTGGGGG ACATTCCACG TTTTCCGCGC CGTAGCTAAC

GCATTAAGTG CCCCGCCTGG GGAGTACGGC CGCAAGGCTA

AAACTCAAAG GAATTGACGG GGGCCCGCAC AAGCGGCGGA

GCATGCGGAT TAATTCGATG CAACGCGAAG AACCTTACCA

AGGCTTGACA TGAACCGGAA TGATGCAGAG ATGTGTCAGC

CACTTGTGGC CGGTTTACAG GTGGTGCATG GTTGTCGTCA

GCTCGTGTCG TGAGATGTTG GGTTAAGTCC CGCAACGAGC

GCAACCCTCG TTCCATGTTG CCAGCGGGTT ATGCCGGGGA

CTCATGGGAG ACTGCCGGGG TCAACTCGGA GGAAGGTGGG

GACGACGTCA AATCATCATG CCCCTTATGT CTTGGGCTTC

ACGCATGCTA CAATGGCCGG TACAAAGGGT TGCGATACTG

TGAGGTGGAG CTAATCCCAA AAAGCCGGTC TCAGTTCGGA

TTGAGGTCTG CAACTCGACC TCATGAAGTT GGAGTCGCTA

GTAATCGCAG ATCAGCAACG CTGCGGTGAA TACGTTCCCG

GGCCTTGTAC ACACCGCCCG TCAAGTCACG AAAGTTGGTA

ACACCCGAAG CCGGTGGCCT AACCCCTTGT GGGAGGGAGC

CGTCGAAGGT GGGACCGGCG ATTGGGACTA AGTCGTAACA AG
```

Thus and according to a particular form of embodiment, the bacterial strain used has a 16S RNA encoded by a sequence having more than 90% or 95% or 99% or even 100% identity with the sequence SEQ ID NO: 1, for example of partial sequence SEQ ID NO: 2.

According to a particular form of embodiment, such an extract contains carotenoids, advantageously is rich in carotenoids.

In the context of the invention, the term "carotenoids" refers to liposoluble pigments characterised by their colour ranging from red to yellow and their absorption spectrum. They belong to the chemical family of terpenoids, with polyunsaturated aliphaticor alicyclic structure.

As mentioned, an extract according to the invention contains carotenoids, which may be membrane-based or cytoplasmic.

Advantageously, and as for example evidenced by HPLC analysis, the extract of the present invention is rich in carotenoids. Carotenoids have a maximum absorption area between 400 and 600 nm, more specifically between 450 and 550 nm, and are identifiable by their absorption spectrum in "3 fingers" at a wavelength close to 490 nm. Even more preferably, carotenoids represent more than 50%, 60%, 70%, 80% or even 90% of the quantity of the extract. Preferably, the extract is free of proteins and/or DNA and/or carbohydrates.

According to a preferred form of embodiment, the extract according to the invention contains different forms of carotenoids, preferably 6 main forms including different isomers or glycosylated forms.

An extract according to the invention is advantageously obtained by culturing *Arthrobacter agilis* under the following conditions:

The culture medium used is typically an LB medium without salt, i.e. containing 1 wt % of tryptone and 0.5 wt % of yeast extract. Alternatively, R2A (Koch et al., 1995, *Int J Syst Bacteriol.* 45(4):837-9) and Bacto Marine 2216 media (Fong et al, 2001, *Appl Microbiol Biotechnol.* 56(5-6):750-6) can be considered.

The cells are preferably cultured at a temperature comprised between 20 and 30° C., for example 25° C.

The growth shall take place in aerobic conditions, preferably under air or oxygen aeration bubble.

The extract according to the invention is preferably obtained from cells in the stationary phase, i.e. typically after 3 days of growth under the conditions described above.

To obtain the extract, the bacterial cells are subjected to an extraction/purification protocol to isolate and purify the carotenoids. Due to the liposoluble nature of carotenoids, obtaining the extract that is the subject matter of the invention preferably relies on the isolation of an apolar phase.

In a first step, the membrane and cytoplasmic components are to be extracted, preferably with the exception of lipids, proteins and DNA. Suitably, a polar solvent is used to "break" the membranes and solubilize a large number of hydrophilic and some lipophilic molecules.

Thus and by way of example, the bacterial pellet can be extracted using acetone, methanol or a mixture of acetone and methanol (for example ⅕ in volume).

In a second step, adding an apolar solvent, preferably hexane, and a saturated aqueous salt solution, preferably a saturated NaCl solution, allows obtaining a biphasic mixture, i.e. an aqueous phase on the one hand and an apolar phase on the other, corresponding to the extract within the scope of the invention. Advantageously, the aqueous phase may be washed, if necessary several times, using the apolar solvent.

The apolar phases are then combined and evaporated under vacuum. The extract thereby obtained can be stored in a cold place, and can be frozen.

It is clear from this method that this is a bacterial extract and not a culture supernatant.

According to a first form of embodiment, the extract according to the invention is used in dry form as powder. Alternatively, the pellet may be included in any suitable lipophilic phase. As part of the cosmetic application according to the invention, the extract is preferably taken in oil, propanediol or a microemulsion.

The carotenoid concentration of the composition reconstituted from the dried extract can be easily measured, for example by measuring the absorbance at 512 nm in DMSO or at 502 nm in propanediol.

Note that the different stages of extraction and purification are preferably carried out away from light, in dark conditions or in half-light, to avoid any deterioration of the extract.

Due to the remarkable properties demonstrated in the context of the present application and discussed below, such an extract can be used particular in a cosmetic composition, a pharmaceutical composition or a dietary supplement.

According to a first aspect, the present invention relates to a cosmetic composition comprising an extract of the bacterium *Arthrobacter agilis*. According to a preferred form of embodiment, the cosmetic composition comprises an extract of the bacterium *Arthrobacter agilis*, which is rich in carotenoids.

The cosmetic composition according to the invention is preferably topical, intended to be applied to the skin and possibly to the hair. It can contain any ingredient or excipient commonly used in cosmetics. In other words, it comprises at least one cosmetically acceptable excipient, all excipients used in such a composition must be cosmetically acceptable.

Note that methanol is not particularly considered a cosmetically acceptable excipient. According to a particular form of embodiment, the cosmetic composition according to the invention therefore does not contain methanol.

It may be in the form of a lotion, cream, gel, spray or in any other form.

According to a particular form of embodiment, it has a pinkish colour.

According to another aspect, the present invention relates to a pharmaceutical composition comprising an extract of the bacterium *Arthrobacter agilis*. According to a preferred form of embodiment, the pharmaceutical composition comprises an extract of the bacterium *Arthrobacter agilis*, which is rich in carotenoids.

The pharmaceutical composition according to the invention may in particular be intended for topical or oral administration. It can contain any ingredient or excipient commonly used in pharmacy. In other words, it comprises at least one pharmaceutically acceptable excipient; all excipients used in such a composition must be pharmaceutically acceptable.

Note that methanol is not particularly considered a pharmaceutically acceptable excipient. According to a particular form of embodiment, the pharmaceutical composition according to the invention therefore does not contain methanol.

It may be in the form of a lotion, cream, gel, spray, or any other form such as drops, capsules, tablets, etc.

Such a pharmaceutical composition may for example be used in the ophthalmic field, especially for treating certain cases of retinopathy (ARMD, etc.), in the treatment of chronic liver diseases or hyperoxia following ischemia-reperfusion. More generally, pathologies in which oxidative stress may permanently damage the proteins are also indicated.

In the same context, a composition according to the invention may be a dietary supplement.

Compositions according to the invention may also contain other active agents, in addition to the extract that is the subject matter of the present invention.

This may include other antioxidants covering different classes of molecules, in particular carotenoids, thiols or phenols.

A non-exhaustive list of such antioxidants, for which a synergistic effect with the extract according to the invention has been demonstrated, is as follows:

Vitamin E or its derivatives, such as Trolox (6-hydroxy-2,5,7,8-tetramethylchroman-2-carboxylic acid);
N-Acetyl-Cysteine (NAC);
Butyl-hydroxy-anisole (BHA);
Vitamin C;
Glutathione;
Caffeic acid or acid (E) 3-(3,4-dihydroxyphenyl) prop-2-enoic acid;
Curcumin or diferuloylmethane;
Quercetin or quercetol;
Lycopene;
Coenzyme Q10 (Q10);
Uric acid.
Plant extracts, such as a green tea extract, a vine shoot extract, an extract of argan tree leaves, a grapefruit extract, a mulberry leaf extract and/or an apple extract, can also be associated with an extract according to the invention.

The concentrations of extract and agent respectively, are determined on a case by case basis by a person skilled in the art, so that the synergy between the two is fully expressed. Thus, the concentrations of the extract and the supplementary agent must be optimised for the antioxidant effect sought.

Preferably, the dry extract represents from 0.00001 ($10^{-5}$) to 0.1 ($10^{-1}$)% i.e. from 0.0001 ($10^{-4}$) to 0.01 ($10^{-2}$)% in weight of the composition according to the invention.

Due to the remarkable properties demonstrated in the context of the present application, such a composition can be used in particular against ageing (anti-ageing effect) or for sun protection (anti-UV effect).

In another aspect, the present invention provides a method of cosmetic treatment, preferably to fight against oxidative stress, in particular cellular ageing of the skin, consisting of applying the cosmetic composition according to the invention on the skin. Oxidative stress can also be caused by exposure to radiation (UV and/or visible), against which the composition according to the invention is particularly effective.

A first possible use of the extract according to the invention is that of a free-radical scavenger, especially vis-à-vis the following free radicals: superoxide radical $O_2.^-$; hydrogen peroxide $H_2O_2$; hypochlorite ion $ClO^-$; hydroxyl radical OH.; peroxide or alkoxy (RO.) radicals (ROO.) wherein R is a carbon chain; the radicals derived from unsaturated fatty acids; peroxynitrite ONOO.; nitrogen monoxide NO.; singlet oxygen $^1O_2$.

An extract according to the invention can also be used as a UV stabiliser, against UV-A (400-315 nm), UV-B (315-280 nm) and/or UV-C (280-153 nm), particularly against UV-C. Remarkably, it has been shown that an extract according to the invention exerted an anti-UV effect through several action mechanisms:

an effect of neutralising oxygen singlets ($^1O_2$) generated by UV;
a "screen", "filter" or "shield" effect by direct UV absorption;
a classic antioxidant effect, i.e. the neutralisation of free radicals generated by oxygen singlet ($^1O_2$).

As already indicated, an extract according to the invention is also beneficial for protection against visible light, in particular blue-violet light (wavelength typically between 400 and 500 nm).

Furthermore, an extract according to the invention has a protective effect on the proteins. Thus, such an extract is capable of stabilising and protecting proteins.

As demonstrated in the present application, this proteome protection shall work in particular vis-à-vis the carbonylation. More generally, this application demonstrates the protective potential of an extract rich in carotenoids on the proteome.

Thus and according to another aspect, the present invention relates to the use of carotenoids for protecting the proteome.

As mentioned above and in view of the synergies demonstrated, the extract according to the invention can be used for these various applications, in combination with other active agents, particularly antioxidants, preferably selected from the following list:

Vitamin E or its derivatives, such as Trolox (6-hydroxy-2,5,7,8-tetramethylchroman-2-carboxylic acid);
N-Acetyl-Cysteine (NAC);
Butyl-hydroxy-anisole (BHA);
Vitamin C;
Glutathione;

Caffeic acid or acid (E) 3-(3,4-dihydroxyphenyl) prop-2-enoic acid;
Curcumin or diferuloylmethane;
Quercetin or quercetol;
Lycopene;
Coenzyme Q10 (Q10);
Uric acid.

EMBODIMENTS

The manner in which the invention can be produced and the advantages resulting from it will be better understood with the embodiments below, given as a rough guide and as part of a non-exhaustive list, with the help of the figures annexed.

FIG. 1 corresponds to an image of inverse microscopy (magnification ×100) of the strain SB5.

1/ISOLATION AND CHARACTERISATION OF THE STRAIN SB5

A bacterium (SB5) was isolated in the falling snow and selected for its resistance to UVC and its ability to grow rapidly. It has been characterised as belonging to arthrobacters, which are positive bacteria grams whose many species are extremophile or extremotolerant.

Specifically, the isolated bacterium is a strain of *Arthrobacter agilis*. *A. agilis* is a non-sporulating and non-pathogenic gram-positive coccoid bacterium, of 0.8 to 1.2 mm in diameter and which may have from 0 to 3 flagella (Koch et al. (1995) *Int J Syst Bacteriol.* 45(4):837-9), isolated for the first time in 1889 (Ali-Cohen (1889) *Zentralbl. Bakteriol. Parasitenkd. Infektionskr. Hyg. Abt.* 1 Orig. 6:33-36).

Figure 1:
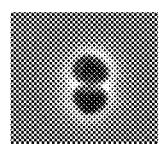

FIG. 1 shows an inverse microscope image of the isolated strain, consistent with the description of the bacterium *Arthrobacter agilis*.

In addition, the fact that the strain SB5 belongs to the species *Arthrobacter agilis* was confirmed by partial sequencing of its 16S RNA. The corresponding sequence (SEQ ID NO: 2) is as follows, the base N indicating that it could not be determined whether the nucleotide corresponded to A, C, G or T:

```
ACATGCAAGT CGAACGATGA ACCTCACTTG TGGGGGGATT
AGTGGCGAAC GGGTGAGTAA CACGTGAGTA ACCTGCCCTT
GACTCTGGGA TAAGCCTGGG AAACCGGGTC TAATACTGGA
TACGACCTTC TGGCGCATGC CATGTTGGTG GAAAGCTTTT
GTGGTTTTGG ATGGACTCGC GGCCTATCAG CTTGTTGGTG
GGGTAATGGC CTACCAAGGC GACGACGGGT AGCCGGCCTG
AGAGGGTGAC CGGCCACACT GGGACTGAGA CACGGCCCAG
ACTCCTACGG GAGGCAGCAG TGGGGAATAT TGCACAATGG
GCGCAAGCCT GATGCAGCGA CGCCGCGTGA GGGATGAAGG
CCTTCGGGTT GTAAACCTCT TTCAGTAGGG AAGAAGCCGG
CCTTTTGGGT TGGTGACGGT ACCTGCAGAA GAAGCGCCGG
CTAACTACGT GCCAGCAGCC GCGGTAATAC GTAGGGCGCA
AGCGTTATCC GGAATTATTG GGCGTAAAGA GCTCGTAGGC
GGTTTGTCGC GTCTGCCGTG AAAGTCCGGG GCTTAACTCC
GGATCTGCGG NGGGTACGGG CAGACTAGAG TGCAGTAGGG
GAGACTGGAA TTCCTGGTGT AGCGGTGAAA TGCGCAGATA
TCAGGAGGAA CACCGATGGC GAAGGCAGGT NTCTGGGCTG
TAACTGACGC TGAGGAGCGA AAGCATGGGG AGCGAACAGG
ATTAGATACC CTGGTAGTCC ATGCCGTAAA CGTTGGGCAC
TAGGTGTGGG GGACATTCCA CGTTTTCCGC GCCGTAGCTA
ACGCATTAAG TGCCCCGCCT GGGGAGTACG GCCGCAAGGC
TAAAACTCAA AGGAATTGAC GGGGGCCCGC ACAAGCGGCG
GAGCATGCGG ATTAATTCGA TGCAACGCGA AGAACCTTAC
CAAGGCTTGA CATGAACCGG AATGATGCAG AGATGTGTCA
GCCACTTGTG GCCGGTTTAC AGGTGGTGCA TGGTTGTCGT
CAGCTCGTGT CGTGAGATGT TGGGTTAAGT CCCGCAACGA
GCGCAACCCT CGTTCCATGT TGCCAGCGGG TTATGCCGGG
GACTCATGGG AGACTGCCGG GGTCAACTCG GAGGAAGGTG
GGGACGACGT CAAATCATCA TGCCCCTTAT GTCTTGGGCT
TCACGCATGC TACAATGGCC GGTACAAAGG GTTGCGATAC
TGTGAGGTGG AGCTAATCCC AAAAAGCCGG TCTCAGTTCG
GATTGAGGTC TGCAACTCGA CCTCATGAAG TTGGAGTCGC
TAGTAATCGC AGATCAGCAA CGCTGCGGTG AATACGTTCC
CGGGCCTTGT ACACACCGCC CGTCAAGTCA CGAAAGTNGT
AACACCCGAA GCCGGNGCCT AACCCCTTGN GGAGGGAGCC
```

This sequence presents effectively more than 99.2% identity with the reference sequence SEQ ID NO: 1, confirming that this strain belongs to the species *Arthrobacter agilis*.

2/PREPARATION OF SBE EXTRACT 2-1. Culture of SB5 Strain:

The strain is cultured in the LB medium without salt at a temperature of 25° C., aerobically and with vigorous stirring, until the stationary phase is reached, after about 3 days.

The cells are then collected by centrifugation, typically at a speed of 5000 rpm for about 15 minutes. The pellet is then dried by storage in the dark at 4° C.

2-2. Isolation of the SBE Extract:

The pellet is taken with 6 ml acetone per gram of pellet, optionally in the presence of methanol, for example in a methanol/acetone mixture (5/1). This extraction step takes place for several hours, typically 18 hours, at 4° C. in the dark.

The suspension in acetone, or in an acetone/methanol mixture, is completed by addition of hexane, preferably at half the volume of acetone. A saturated solution of NaCl (sodium chloride) is then added until the separation of the biphasic mixture, with an aqueous phase on one hand and an apolar phase on the other. Preferably, the aqueous phase is again extracted using hexane and the hexane phases are combined.

The apolar or hexane phase is evaporated, preferably under vacuum at 25° C.

The SBE extract can be preserved as is at −20° C. or may be taken as a solution, for example in the DMSO (dimethylsulfoxide) or THF (tetrahydrofuran) or propanediol to be tested on live cells, and is highly soluble in dichloromethane and acetone.

The carotenoid concentration is determined by measuring the absorbance at 512 nm in DMSO or 502 nm in propanediol.

Figure 2:
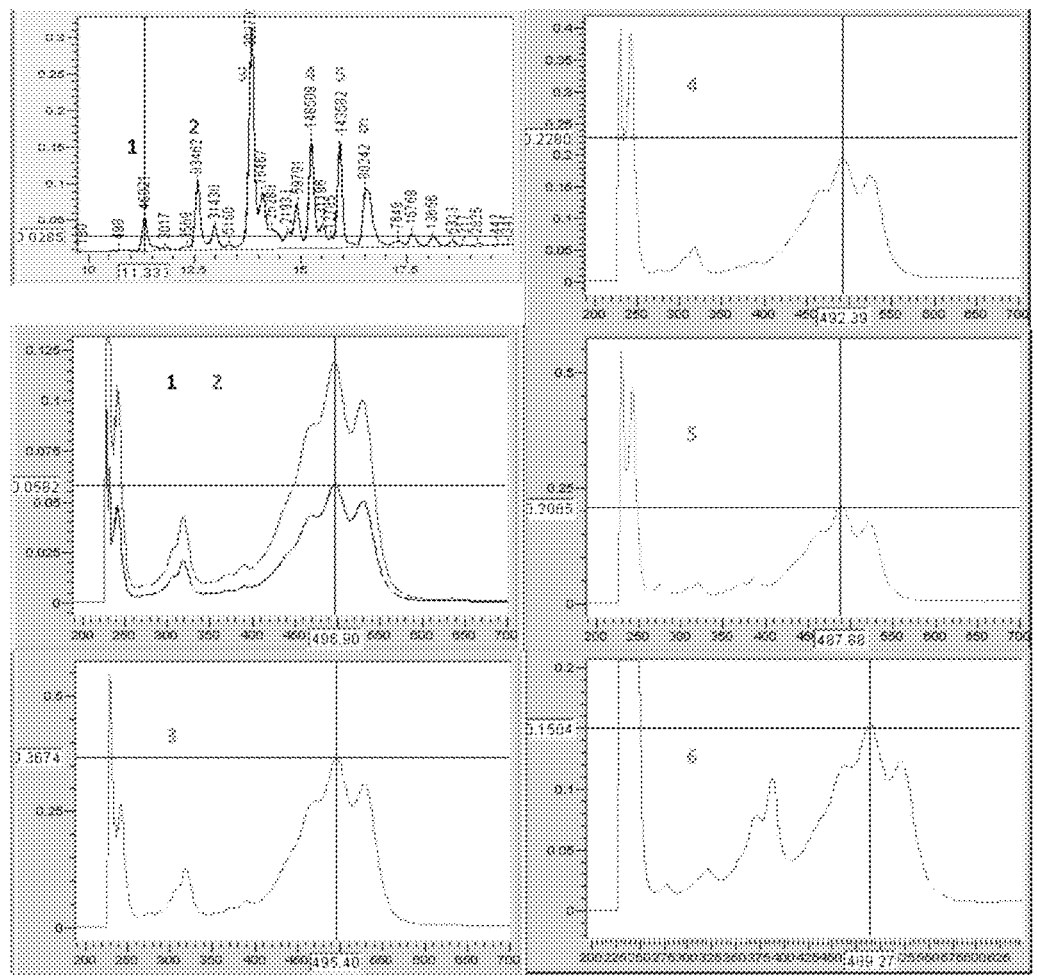
FIG. 2 shows the HPLC spectrum of the SBE extract according to the invention and the absorbance spectrum for each of the six main peaks (graded 1 to 6).

The HPLC spectrum of the extract and the absorbance spectrum for each of the six main peaks are shown in FIG. 2. Comparison of these spectra with the literature data (Fong et al, *Appl Microbiol Biotechnol* (2001) 56: 750-756) showed that the extract contains significant quantity of carotenoids, with a characteristic absorption spectrum of 3 "fingers" to 490 nm. As described in Fong et al, (*Appl Microbiol Biotechnol* (2001) 56: 750-756), the absorption spectrum also revealed the presence of glycosylated forms and different isomers of these carotenoids.

3/ACTIVITIES OF THE SBE EXTRACT 3-1. ABTS Assay:

As mentioned above, this assay is conventionally used in the cosmetics and agri-food industry helps establish, in a purely chemical manner, the "total antioxidant capacity" of an extract. Although this assay is incomplete because it measures the antioxidant activity of the extract only when dealing with a particular kind of radical, it has the advantage, by way of its standardisation with Trolox, of generating results that are comparable with thousands of other molecules tested in this manner.

This assay was carried out as described in Re et al., *Free Radic. Biol. Med.* (1999) 26(9-10): 1231-7.

Figure 3:
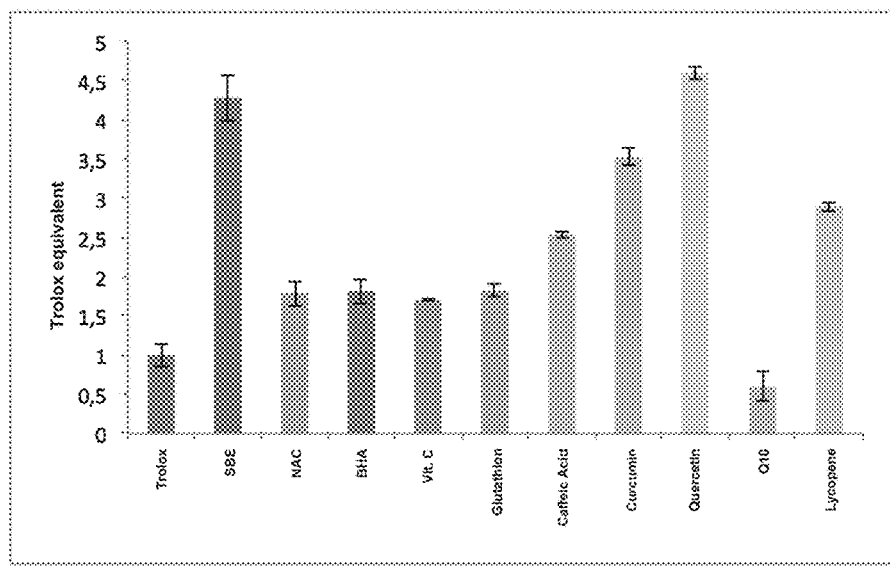
FIG. 3 shows the antioxidant power measured using the ABTS assay of the extract according to the invention (SBE) relative to other known antioxidants, expressed as Trolox equivalent.

FIG. 3 shows that the extract according to the invention (SBE) shows antioxidant capacity over 4 times higher than that of the reference antioxidant, Trolox.

In the context of the invention, a Trolox equivalent corresponding to the number of moles of the product tested helps obtain an effect equivalent to that of 1 mol Trolox. The extract according to the invention was quantified with the use of carotenoids as a marker of the extract. Thus, 1 mol of the SBE extract corresponds to 1 mole of carotenoids as measured by absorbance at a wavelength corresponding to the maximum absorption and deducted from the molar extinction coefficient of the carotenoids.

3-2. Protection of Proteins Against Free Radicals:

This test consists of measuring at 405 nm the activity of alkaline phosphatase (AP) in the presence of free radicals, especially hydroxyl (OH.), and a compound or extract, in order to assess the protective capacity vis-à-vis the proteins of the said compound or extract.

Materials and Methods:

Reagents:

Buffer: "Tris Buffered Saline" powder (Sigma; Product reference: T6664-10PAK);

Enzyme: Alkaline phosphatase 10 KU at 125 U/4 in buffered glycerol solution (Sigma; Product reference: P0114);

Oxidizing Agent:

1/Hydrogen Peroxide at 30% or 9M (Sigma; Product reference: H1009-5ML): solution B1;

2/Iron II sulphate heptahydrate ($FeSO_4$, $7H_2O$) 0.1M (Fluka; Product reference: 44970): solution B2;

Substrate: solution of 4-nitrophenyl phosphate ("Alkaline Phosphatase yellow substrate"; Sigma; Product reference: P7998-100ML).

Kit:

96-well plate;

Buffer: 20 ml of a TBS solution—0.05 M, pH 8;

Solution A (enzyme): 10 µl of the stock solution diluted at 1/1000 (or 1.25 U i.e. 0.125 U/µL) in the buffer;

100 µl of solution B1 and 100 µl of solution B2 or solution B corresponding to the mixture of solutions B1 and B2 at a suitable dilution in the buffer (for example 3 ml of solution B at 90 mM, obtained from 30 µl of solution B1+30 µL of solution B2 i.e. a 1/100 dilution);

Solution C (substrate): 5 ml of the commercial solution.

Protocol:

Dilute the solution A in the buffer at a suitable dilution;

Insert, in each well, 10 µl of the diluted solution A so as to have an enzyme amount between 0.005 to 0.05 U;

Add 10 µl of the product or the extract to be tested, optionally diluted in the buffer in each well. The individual wells can be used to test a range of dilution;

Add 30 µl of solution B to each well. The concentration of the solution B is adjusted to obtain 90% inactivation of the amount of enzyme present. The final concentration of the oxidising agent equal to 30% of the concentration of the solution B;

Incubate for 15 minutes at 37° C. without stirring;

Add 50 µl of solution C. The reaction volume is thus equal to 100 µl;

Place the plate at 37° C. with stirring;

Read the absorbance at 405 nm for 20 minutes (kinetic) or after 5 minutes of reaction (selective).

Results

Figure 4A:
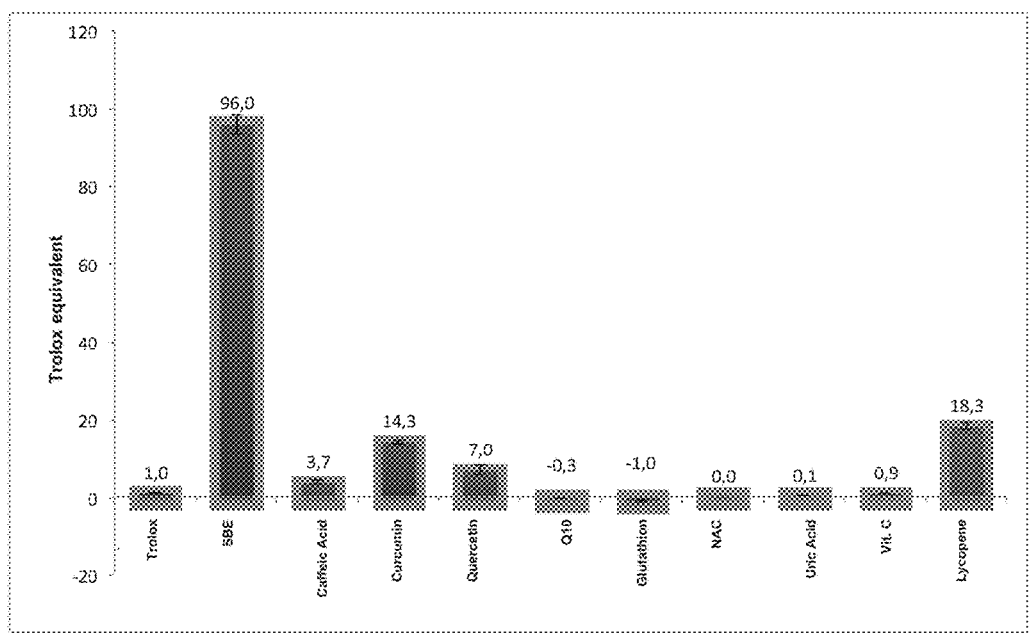
FIG. 4 shows the protective capacity of proteins, vis-à-vis the free radicals, of the extract according to the invention (SBE) compared to other antioxidants, expressed as Trolox equivalent (A), and compares this protective capacity to that of the fractions corresponding to the 6 peaks observed in HPLC (B).

FIG. 4A shows that the extract according to the invention (SBE) has a protective capacity of proteins, against free radicals, about 100 times higher than that of the Trolox, and more than 6 times higher than all the antioxidants tested. The difference between this result and the antioxidant potential measured by ABTS demonstrates that the protection of proteins is not linked only to the antioxidant potential of SBE.

Furthermore, the same technique was used to compare the effect of 6 fractions (graded SB1 to SB6) corresponding to the 6 major peaks identified by HPLC analysis to that of the total extract SBE.

Figure 4B:
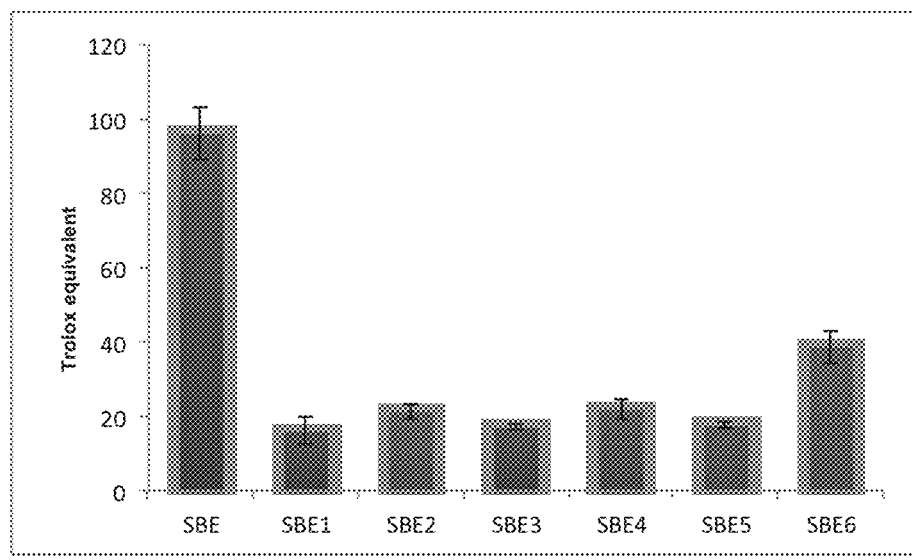

It is clear from FIG. 4B that the SBE extract has a protective capacity against free protein radicals which is 2 to 4 times higher than that of each of the peaks that it comprises and demonstrates a synergistic effect between the various fractions of the extract.

3-3. Protection of Proteins Against UV:

This test is similar to that described in the previous section. It consists of measuring at 405 nm the activity of alkaline phosphatase (AP), irradiated using UV-C (254 nm), in the presence of a compound or an extract, in order to assess the protective capacity vis-à-vis the proteins of the said compound or extract.

Materials and Methods:

The alkaline phosphatase was subjected to UV radiation at 254 nm corresponding to the UV-C. Under constant stirring, the UV doses resulting in 90% inactivation of the enzyme were applied to a reaction medium and under conditions similar to those mentioned above. Note that the volume occupied by the oxidising agent is replaced with the buffer. In practice, a lamp with a power equal to 0,0365 $J/cm^2/min$ a lamp, with an exposure time of 1 or 2 hours.

Results

Figure 5:
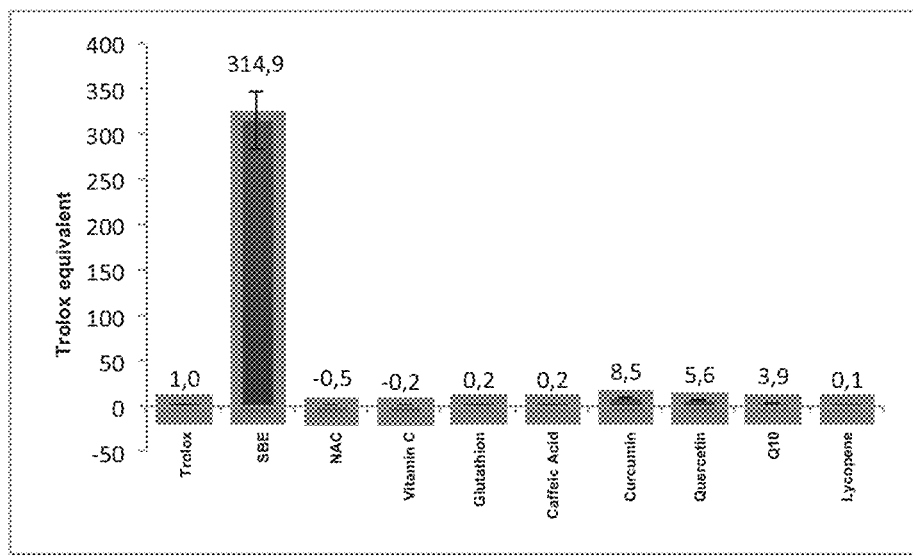
FIG. 5 shows the protective capacity of proteins, vis-à-vis the UVs, of the extract according to the invention (SBE) compared to other antioxidants, expressed as Trolox equivalent.

FIG. 5 shows that the extract according to the invention (SBE) has a protein protection capacity against UV, which is more than 300 times higher than that of the Trolox and almost 40 times greater than all the antioxidants tested.

This very strong protective capacity of the extract according to the invention may be explained by several combined effects of the extract in the presence:

- an effect of neutralising oxygen singlets ($^1O_2$) generated by UV;
- a "screen", "filter" or "shield" effect by direct UV absorption;
- a classic antioxidant effect, i.e. the neutralisation of free radicals generated by oxygen singlet ($^1O_2$).

3-4. Protection of Proteins:

The activity of alkaline phosphatase was measured in the absence of oxidative stress but in the presence of increasing concentrations of the extract according to the invention (SBE).

Figure 6:
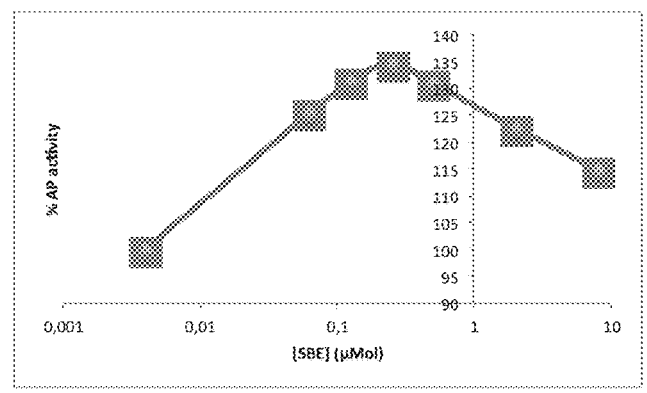
FIG. 6 shows the monitoring of the activity of the alkaline phosphatase (AP) depending on the concentration of the extract according to the invention (SBE).

FIG. 6 shows that the AP activity increases in the presence of the extract according to the invention (SBE) at very low doses. This increase may be due to the protection of the enzyme during incubation and agitation. It is also conceivable that some of the oxidation of the enzyme stored at −20° C. is reduced by the SBE extract, which could increase its activity by "rejuvenation".

On the basis of FIG. 6, a suitable concentration of the extract according to the invention (SBE) is between 0.001 and 100 μm, preferably between 0.1 and 1 μM. However, these are concentrations to be achieved in the target cells of the skin. Thus, the concentration in the cosmetic compositions must be much higher to account for the losses related to skin penetration.

An interaction between the enzyme and the extract could be the cause of this "boosting" action. By extension, the extract according to the invention is likely to protect the proteins in the body, especially those directly involved in protecting the body against oxidative stress or in the repair of oxidative damage.

3-5. Synergy with Other Antioxidants:

To identify antioxidants that may increase the effectiveness of the protein protection by the extract according to the invention (SBE), the test described in the section 3-2 was carried out by mixing the extract according to the invention (SBE) and a dozen known antioxidants, taken individually. It is necessary to identify molecules with which the extract according to the invention (SBE) combines the antioxidant effects or to highlight synergies beyond additive effects. Another advantage of such mixtures is the possible stabilisation of the extract according to the invention (SBE).

Figure 7:
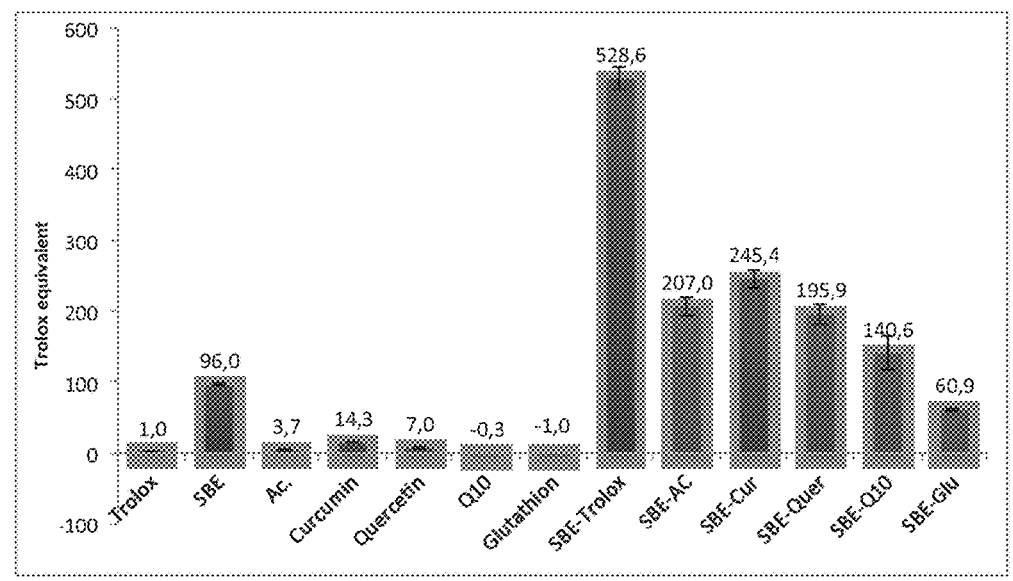
FIG. 7 shows the protective capacity of proteins, vis-à-vis the free radicals, of the extract according to the invention (SBE) mixed with other antioxidants, expressed as Trolox equivalent.

FIG. 7 shows that in the presence of all the antioxidants tested, and especially in the presence of Trolox, the extract according to the invention (SBE) has a strong synergy, which significantly increases (by a factor of 5 with Trolox) its protein protection capacity against free radicals.

3-6. Protection of Human Cells:

A/Comet Assay:

To confirm the protection by the extract according to the invention (SBE) of human cells, measures to protect primary cultures of keratinocytes and their DNA facing oxidative stress induced by UV/visible light were implemented through the comet assay, as described by Ostling, O., and K. J. Johanson. (*Biochemical and biophysical research communications* 123.1 (1984): 291-298) and Singh, Narendra P., et al. (*Experimental cell research* 175.1 (1988): 184-191). It is essential to show the protection activity of the extract according to the invention (SBE) in a cell model and compare it to a reference antioxidant, tocopheryl acetate.

Materials and Methods:

The antioxidant properties of the SBE and tocopherol acetate (Ac-Toc) against UVB/UVA/VISIBLE radiation (Irradiated: 290 nm-800 nm) were assessed by the comet assay (alkaline version) on primary cultures of normal human keratinocytes.

The antioxidant properties were evaluated at concentrations of 500 nM for SBE and 50 μM for Ac-Toc. Both products were dissolved in tetrahydrofuran at a final concentration of 1%. The antioxidant properties have been defined as the ability to reduce the number of single-stranded breaks of the DNA of cells which occur after UVB/UVA/visible radiation (290-800 nm) and these properties were measured after contact with the products for 120 minutes at 37° C. The radiation was delivered by a solar simulator Suntest CPS+ (Atlas Material Testing Technology BV, Moussy le Boeuf, France). The total radiation dose was 12.0 J/cm2 for a period of 2.7 minutes (rated power of the lamp—750 W/m2). Negative controls included non-irradiated keratinocytes treated by THF (1%) and by Ac-Toc (50 μM) and SBE (500 nM) in 1% THF.

Results

Figure 8:
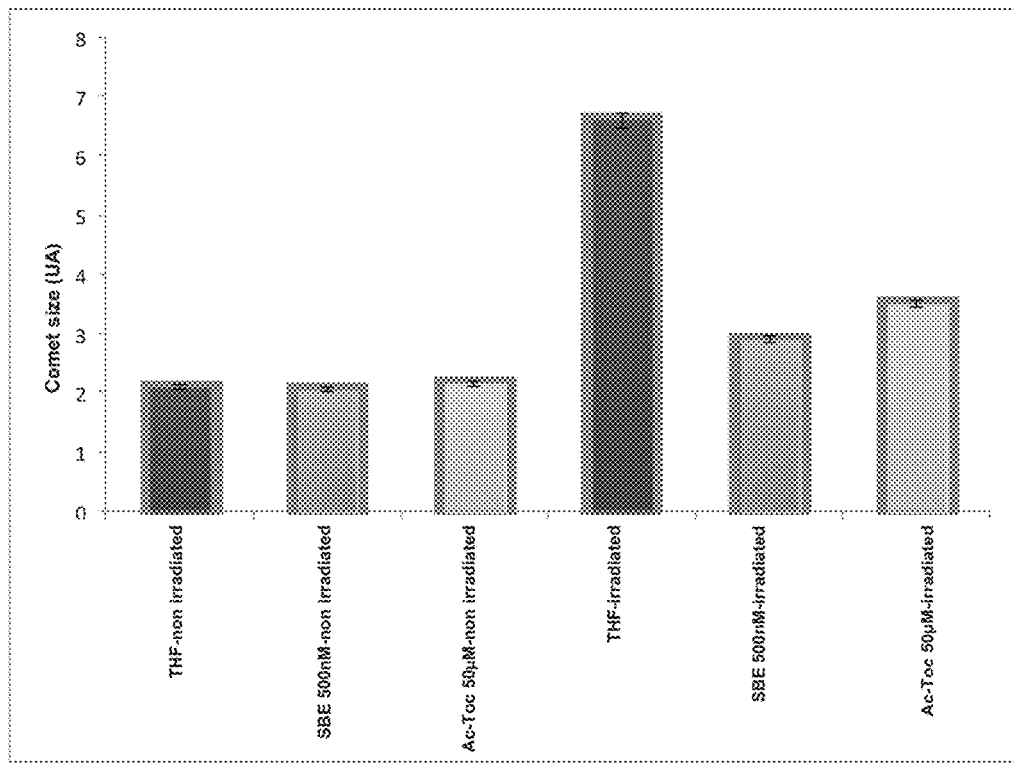
FIG. 8 shows the protective capacity of human cells (keratinocytes) and their DNA, vis-à-vis free radicals and UVs, of the extract according to the invention (SBE) relative to tocopheryl acetate using the comet assay.

FIG. 8 shows that the extract according to the invention (SBE) has a high cell protective capacity against oxidative stress and that it helps to protect cell DNA better than Tocopherol acetate, while being 100 times less concentrated. Its in vitro protective capacity is thus over 100 times greater than that of tocopherol acetate.

B/Carbonylation Test:

By following the same UV/visible irradiation protocol as the one used above for the comet assay, the rate of carbonylation of keratinocytes in the presence of SBE and tocopherol acetate was measured.

Materials and Methods:

1—Culture of Keratinocytes and Irradiation

Normal human keratinocytes (NHK) (T6)-$10^6$ cells/condition

Conditions:
1% THF solvent control
SBE 200 nM
Tocopherol acetate 20 μM

Each condition is carried out in triplicate.

Contact with KHNs in different experimental conditions for 2 hours.

UVB/UVA/Visible irradiation at 120 kJ/m$^2$ of the cells placed in PBS by a Suntest CPS+ solar simulator (Atlas Material Testing Technology) at 4° C. Negative controls are maintained at 4° C. for the same duration as the irradiation.

Trypsination of the cells post irradiation. Rinsing of the iced PBS. Elimination of the PBS and immediate freezing of the cell pellets at −80° C.

2—Measurement of the Carbonylation

The proteins are extracted after lysis of the cells and their concentration is measured using the Bradford test.

The proteins are derived by 2,4-dinitrophenylhydrazine (DNPH), which binds to the carbonyl groups.

The carbonylation rate is then measured on ELISA plates (OxyELISA™ Oxidized Protein Quantitation Kit, Millipore) at 450 nm.

Results

Figure 9:
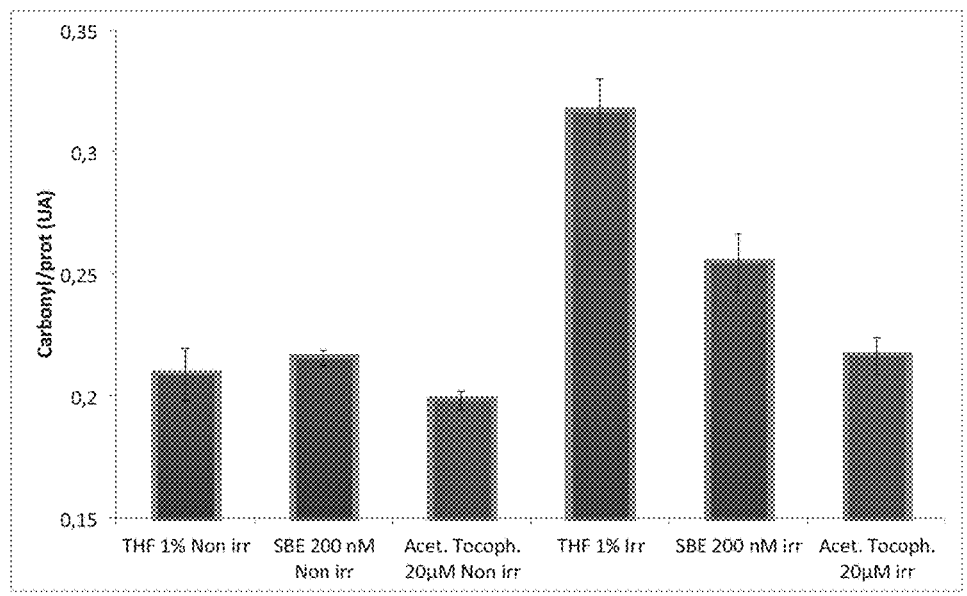
FIG. 9 shows the measurement of protein carbonylation evaluating the protective capacity of human cells (keratinocytes) and their proteins, vis-à-vis UV/visible light radiation, of the extract according to the invention (SBE) compared to tocopherol acetate.

FIG. 9 shows that the rate of carbonylation of proteins of the keratinocytes significantly increases after UV/visible irradiation. This increase decreases significantly (P-value <0.01) by the addition of the SBE extract or tocopherol acetate which protects the protein against oxidation. This protection is similar (P-value>0.01) for SBE and tocopherol acetate although the SBE extract is 100 times less concentrated.

Although slightly less strong, the proteome protection capacity of the SBE is the same as that observed through the comet assay and 100 times that of tocopherol acetate, which corresponds to the results obtained below based on the measurement of the activity of alkaline phosphatase (AP).

The protection of cells observed using the comet assay seems mainly driven by the ability of SBE to protect the proteome.

4/COSMETIC COMPOSITION OF THE SBE EXTRACT

The cosmetic compositions typically comprise from 0.0001 to 0.01 wt % of the extract (dry) according to the invention.

A cream can have the following composition (% by weight), the agent comprising the extract according to the invention being preferably integrated into isononyl isononanoate.

| INCI Name | % by weight |
|---|---|
| Aqua | 78.290000 |
| Xanthan Gum | 0.100000 |
| Ammonium Acryloyldimethyltaurate/ VP Copolymer & Aqua | 0.800000 |
| Glycerin | 5.000000 |
| Butylene Glycol | 2.000000 |
| Phenoxyethanol | 0.350000 |
| Disodium EDTA | 0.200000 |
| Chlorphenesin | 0.260000 |
| Steareth-21 | 1.160000 |
| Steareth-2 | 1.840000 |
| Dimethicone | 2.000000 |
| Glyceryl Dibehenate & Tribehenin & Glyceryl Behenate | 0.500000 |
| Isononyl Isononanoate | 5.000000 |
| Acacia Decurrens/Jojoba/Sunflower Seed Wax/Polyglyceryl-3 Esters | 1.000000 |
| Cetyl Alcohol | 1.500000 |

Typically, these compositions may have a colour ranging from light pink to red, because of the colour of the extract according to the invention.

These embodiments show that the particular choice of the bacterium *Arthrobacter agilis* as a source of carotenoids (found in many species, including algae plants, cyanobacteria, fungi, etc.) has unexpected benefits within the context of the applications:

Relatively easy culturing of the bacterium and preparation of the extract (unlike many extremophile organisms including halobacter);

Synergy between the different fractions of the extract;

Contribution of different isoforms in the overall activity of the extract (unlike for example the only deinoxanthin of *Deinococcus radiodurans*);

Very strong anti-radical and anti-UV activity relative to known antioxidants;

Synergy with known antioxidants;

Protective effect never revealed vis-à-vis the proteome, which goes beyond the antioxidant capacity: The antioxidant capacity of SBE extract is 4 times higher than that of Trolox, while its capacity to protect the proteins is 100 times stronger than that of Trolox, in the context of both biochemical tests as well as cell cultures.

---

The invention claimed is:

1. A cosmetic, pharmaceutical, or dietary composition comprising:
   (a) an extract rich in carotenoids of the bacteria *Arthrobacter agilis* and
   (b) vitamin E or a derivative of vitamin E.

2. The composition according to claim 1, wherein the extract is obtained by culturing the bacterium in a medium consisting of 1 wt % of tryptone and 0.5 wt % of yeast extract.

3. The composition according to claim 1, wherein the extract is obtained from cells in the stationary phase.

4. The composition according to claim 1, wherein the extract corresponds to an apolar phase obtained from bacterial cells precipitated after being cultured in a culture medium.

5. The composition according to claim 4, wherein the apolar phase is obtained by adding an apolar solvent and a saturated salt solution to the precipitated bacterial cells.

6. The composition according to claim 5 wherein the bacterial cell precipitate is extracted using acetone and/or methanol.

7. The composition according to claim 5, wherein the apolar solvent is hexane.

8. The composition according to claim 5, wherein the saturated salt solution is a NaCl solution.

9. The composition according to claim 1, wherein the vitamin E derivative is trolox (6-hydroxy-2,5,7,8-tetramethylchroman-2-carboxylic acid), or tocopherol acetate.

10. The composition according to claim 1, wherein the extract represents from 0.0001 to 0.01% by dry weight of the composition.

11. The composition according to claim 1, wherein the composition is in the form of a lotion, cream, gel, spray, solutions, capsules or tablets.

12. The composition according to claim 1, further comprising an antioxidant.

13. The composition according to claim 12, wherein the antioxidant is selected from the group consisting of;
   N-acetyl-cysteine (NAC);
   butyl-hydroxy-anisole (BHA);
   vitamin C;
   glutathione;
   caffeic acid or (E) 3-(3,4-dihydroxyphenyl)prop-2-enoic acid;
   curcumin or diferuloylmethane;
   quercetin or quercetol;
   lycopene;
   coenzyme Q10 (Q10); and
   uric acid.

14. The composition of claim 1, comprising the extract rich in carotenoid of the bacteria *Arthrobacter agilis* and vitamin E.

* * * * *